United States Patent [19]

Desmond et al.

[11] Patent Number: 4,871,873
[45] Date of Patent: Oct. 3, 1989

[54] PROCESS FOR SYNTHESIS OF ARYLGLYOXAL ARYLIMINES

[75] Inventors: Richard Desmond, Metuchen; Sander G. Mills, Woodbridge; Ralph P. Volante, East Windsor; Ichiro Shinkai, Westfield, all of N.J.

[73] Assignee: Merck & Company Incorporated, Rahway, N.J.

[21] Appl. No.: 169,649

[22] Filed: Mar. 18, 1988

[51] Int. Cl.$^4$ ............................................. C07C 131/00
[52] U.S. Cl. .................................. 564/276; 564/277; 564/271; 568/316
[58] Field of Search ................ 568/316, 216; 564/277, 564/271

[56] References Cited

U.S. PATENT DOCUMENTS 3,385,894  5/1968  Schipper ............................. 568/316
4,131,686  12/1978  Ikezaki et al. ...................... 564/276
4,276,304  6/1981  Ikeyaki et al. ...................... 564/276

OTHER PUBLICATIONS

Alcaide et al., Chem. Abst., vol. 101, #130313 U (1984).
Prato et al., Chem Abst., vol. 102, #131597 X (1985).
Furukawa et al., J. Chem. Soc., Perkin I, pp. 372–377, (1977).
Shipper et al., Tet. Letter, pp. 6201–6206 (1968).
Feisin et al., "Reagents for Org. Synthesis", vol. 2, pp. 160–161 (1988).
Kornblum et al., J. Am. Chem. Soc., 79, p. 6562 (1957).

*Primary Examiner*—James H. Reamer
*Attorney, Agent, or Firm*—Robert J. North; Joseph F. DiPrima

[57] ABSTRACT

A process for producing arylglyoxal arylimine intermediates, by the DMSO/HBr oxidation of arylmethylketones. The imine compounds are intermediates in the synthesis of carbapenem antibiotics, i.e. imipenem.

14 Claims, No Drawings

PROCESS FOR SYNTHESIS OF ARYLGLYOXAL ARYLIMINES

BACKGROUND OF THE INVENTION

(1) Field of the Invention

This invention relates to an improved general process for producing arylglyoxal arylimine intermediates by the oxidation of aryl methylketones which are useful in carbapenem antibiotic synthesis.

(2) Brief Description of Disclosures in the Art

Carbapenem antibiotics, particularly thienamycin and imipenem (see U.S. Pat. Nos. 3,950,377 and 4,194,047) are well known for treating a broad spectrum of gram-negative and gram-positive bacterial infections.

Processes for synthesis of these type antibacterial agents are well known in the art as witness the following patents issued inter alia to Merck & Co.; U.S. Pat. Nos. 4,543,257, 4,234,596 and 4,232,030.

In order to develop, faster, less expensive and better methods for their production, research is continually being carried out in this area. One focus in this field has been on different modes for the synthesis of the starting azetidinone intermediates.

For example, the one-step cycloaddition of an imine and a ketene to product azetidinones is well known in the art, e.g. H. Staudinger and S. Jologin, Chem. Ber., 1911, 44, p. 373.

Since the discovery of (3R,4R)-3-[(1R)-1-hydroxyethyl]-4-acetoxyazetidin-2-one (1) (see Scheme I) as a key intermediate for the synthesis of the carbapenems thienamycin and methyl thienamycin an intensitve effort has been directed towards the development of a selective and cost-efficient synthesis of 1 or its 4-aroyl precursor 6. (See: Reider, P. J.; Grabowski, E. J. J.; Tetrahedron Lett. 1982, 2293; Ito, Y.; Terashima, S.; Tetrahedron Lett. 1987, 6625; Fuentes, L. M., Shinkai, I., Salzmann, T., J. Am. Chèm. Soc. 1986, 108, 4673; Ito, Y., Kawabata, T., Terashima S., Tetrahedron Lett. 1986, 5751; Hart, D. J., Ha, D. C., Tetrahedron Lett. 1985, 5493.) It has recently been demonstrated that 4-aroyl-2-azetidinone 6 is readily available via cycloaddition of 3(S)-triisopropylsilyloxybutyryl chloride 4 with p-anisidine 1,2-iminoketone 5 in the presence of a tertiary amine base such as triethylamine. (See: Alcaide, B., Dominquez, G., Parreno, V., Plumet, J., Heterocycles, 1986, 24, 6).

SCHEME I

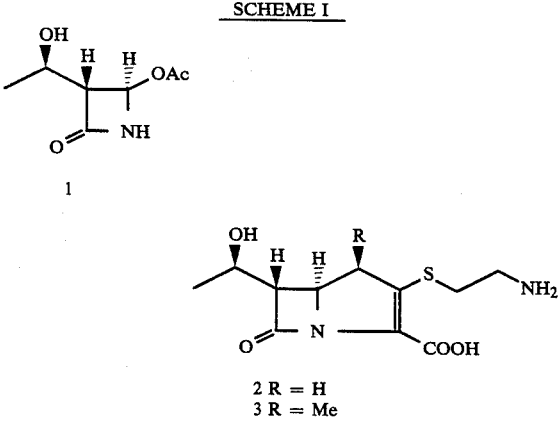

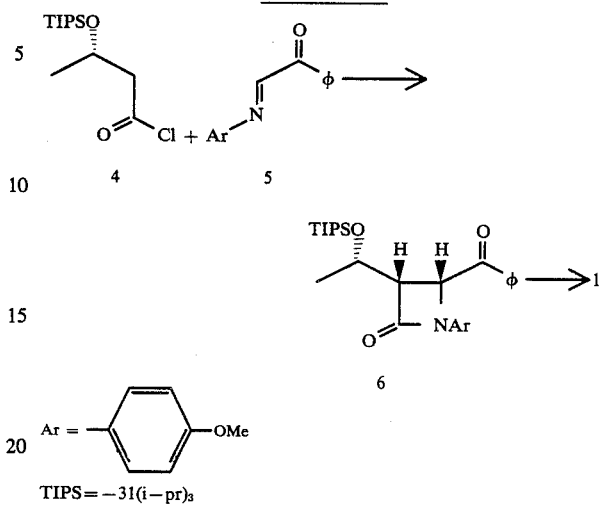

The 1,2-iminoketone 5 was previously prepared from phenylglyoxal monohydrate and p-anisidine via standard methodology (see Alcaide et al. supra). However, due to the prohibitively high cost of phenylglyoxal monohydrate people in the art are interested in the development of an alternative, more cost-effective methodology for its synthesis that would be applicable for large scale production of imine 5.

It has been known for some time that active carbonyl compounds are oxidized to 1,2 dicarbonyl compounds by dimethyl sulfoxide in the presence of hydrogen halides. For example, Schipper and co-workers have described the use of aqueous HBr in dimethyl sulfoxide for the oxidation of 1,3-diketones to 1,2,3-triketones. (See Schipper, E., Cinnamon, M., Rascher, L., Chiang, Y. H., Oroshnik, W., Tetrahedron Lett. 1968, 6201.) However, the yield for the oxidation of acetophenone to phenylglyoxal was reported to be only 10%. Similarly, Furukawa, et al. (see Furukawa, N., Akasaka, T., Aida, T., Oae, S.; J. Chem. Soc. Perkin I. 1977, 372) employed iodine, dimethyl sulfoxide, and sulfuric acid for analogous oxidations of several active methylene systems; however, only traces of phenylglyoxal were obtained when acetophenone was used as the substrate.

SUMMARY OF THE INVENTION

We have found that acetophenone can be readily oxidized with dimethylsulfoxide in the presence of hydrobromic acid to generate a crude solution of phenylglyoxal (see Scheme II). The phenylglyoxal thus prepared is not isolated but can be converted directly to the desired imine 5 by treatment with p-anisidine in the presence of a drying agent or water scavenger, for example, molecular sieves. The resulting anhydrous solution of 5 (after a brief aqueous work-up and drying) can be used directly in subsequent ketone cycloaddition reactions, or the imine 5 can be isolated as an oil after concentration in vacuo (71% yield from acetophenone).

The process has general applicability to the synthesis of arylglyoxal arylimines.

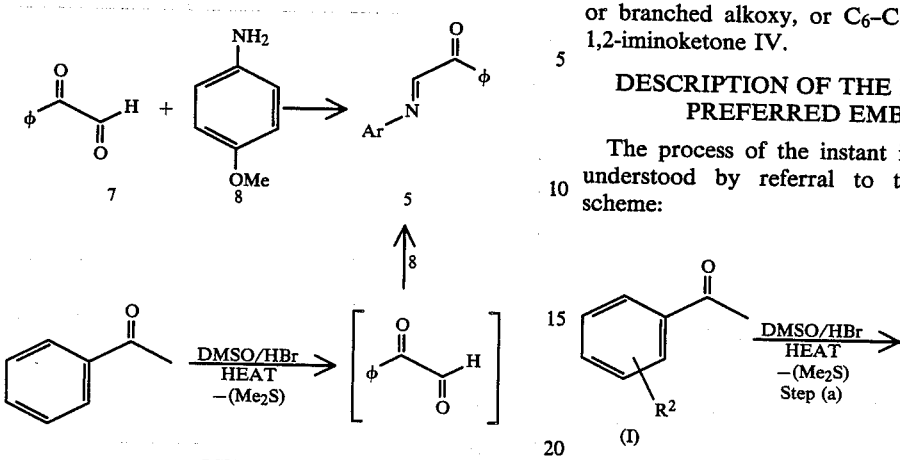

SCHEME II

By this invention there is provided a process for preparing the 1,2-iminoketone

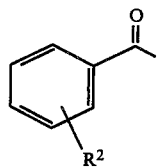 (IV)

comprising the steps of
(a) contacting the arylketone

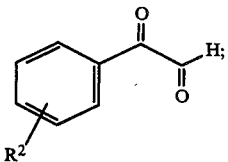 (I)

wherein $R^2$ is H, $C_1$-$C_4$ linear or branched alkyl, $C_6$-$C_8$ aryl, benzyl, nitro, halo, trifluoromethyl, $C_1$-$C_4$ linear or branched alkoxy, or $C_6$-$C_8$ aryloxy, with aqueous HBr in DMSO solvent, at a temperature in the range of 50° to 150° C., thereby evolving DMS gas, for a sufficient time to substantially form the glyoxal II:

(II)

(b) contacting said glyoxal II from step a) with an aromatic amine III:

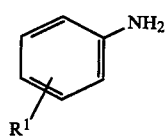 (III)

where $R^1$ is hydrogen, $C_1$-$C_4$ linear or branched alkyl, $C_6$-$C_8$ aryl, benzyl, halo, trifluoromethyl, $C_1$-$C_4$ linear or branched alkoxy, or $C_6$-$C_8$ aryloxy, to form said 1,2-iminoketone IV.

DESCRIPTION OF THE INVENTION AND PREFERRED EMBODIMENTS

The process of the instant invention can be easily understood by referral to the following reaction scheme:

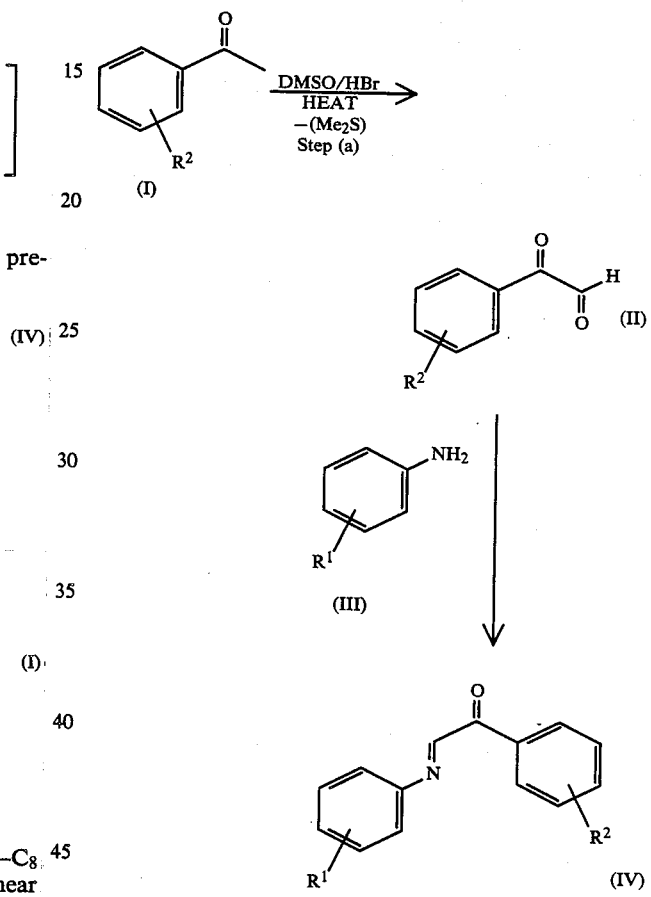

Starting aryl methyl ketone I can have substituent $R^2$ as H, $C_1$-$C_4$ linear or branched alkyl, $C_6$-$C_8$ aryl, benzyl, nitro, halo, trifluoromethyl, $C_1$-$C_4$ linear or branched alkoxy or $C_6$-$C_8$ aryloxy. $R^2$ is either a meta or ortho substituent, inert under the reaction conditions, or the ring can be mono, di, or trisubstituted by $R^2$, e.g. 3-substituted acetophenone, 3,4-disubstituted acetophenone, 3,4,5-trisubstituted acetophenone. Representative examples of I include acetophenone, p-chloroacetophenone, p-fluoroacetophenone, m-chloroacetophenone, p-methoxyacetophenone, p-trifluoromethylacetophenone, m-nitroacetophenone, p-methylacetophenone, p-t-butylacetophenone, p-phenylacetophenone, m-benzylacetophenone, p-methoxyacetophenone, p-phenoxyacetophenone, and the like. Said substituent $R^2$ is inert under the reaction conditions. Preferred substituent is hydrogen, wherein the molecule is acetophenone.

The arylmethyl ketone is heated in step a) in a dimethylsulfoxide (DMSO) solution containing hydrobromic acid.

The concentration of the arylmethyl ketone in the DMSO solvent is about 1 to 5 moles/liter and preferably 2 to 2.5 mols/liter.

The HBr used can be anhydrous, or in aqueous form. The molar ratio of HBr to the arylmethyl ketone is about 0.5 to 1.0 and preferably 0.75. Preferably, aqueous HBr (48%) is used.

The solution is stirred by conventional means and heated to a temperature of about 50° to 150° C., preferably 70° to 80° C., to initiate the evolution of byproduct dimethylsulfide (DMS). The DMS can be vaporized off or distilled under a column to remove it from the reaction mixture. The boiling point of DMS is 35°–40° C. (1 atmosphere).

The reaction can be conducted under a pressure of 1 atmosphere or under reduced pressure to about 0.05 atmospheres. Atmospheric pressure is preferred.

The heating is continued and the progress of the reaction monitored, for example, by high pressure liquid chromatography (HPLC) following the rate of disappearance of the starting arylmethylketone as indicated by a characteristic retention time.

Generally, the yields of the glyoxal II are best where the reaction is stopped when 98–99% of the theoretical amount of glyoxal is formed, i.e. 98–99% of the starting acylmethylketone has been consumed. Further heating leads to undesired byproduct formation and lower yields. A decrease in the amount of DMS generated will be observed during this period.

The reaction solution at this point is cooled. The glyoxal can be isolated by conventional means, but preferably the reaction solution is mixed with an inert, water-immiscible organic solvent to dilute the in situ formed glyoxal II.

Representative examples of classes of diluting solvents are $C_1$–$C_8$ linear or branched alkanes, $C_5$–$C_8$ cyclic alkanes, wherein said alkanes can be mono- to hexahalogenated alkanes, $C_2$–$C_8$ linear ethers and cyclic ethers and $C_6$–$C_8$ aromatic hydrocarbons.

Representative examples of specific solvents are methylene chloride, carbon tetrachloride, chloroform, hexane, cyclohexane, diethyl ether, benzene, toluene, or xylenes. Preferred are the halogenated alkanes, particularly chlorinated alkanes, and particularly preferred is methylene chloride.

Following the mixing of solvents, the aqueous phase is separated, and the resulting organic phase is dried using a solid drying agent such as sodium sulfate, magnesium sulfate, and the like. Preferred is sodium sulfate.

The organic solution is then treated with a solid basic reagent to neutralize traces of acid. Generally a reagent that can be used is solid sodium bicarbonate, sodium hydroxide, calcium hydroxide, potassium carbonate, and the like, with sodium bicarbonate being preferred.

To the organic solution is then added a further drying agent to remove water during the subsequent imine formation. Generally reagents that can be used are 3A molecular sieves, calcium sulfate, magnesium sulfate and the like, with the molecular sieves being preferred.

The aromatic amine is then added, wherein $R^1$ is either a meta or para substituent, inert under the reaction conditions, being hydrogen, $C_1$–$C_4$ linear or branched alkyl, $C_6$–$C_8$ aryl, benzyl, nitro, halo, trifluoromethyl, $C_1$–$C_4$ linear or branched alkoxy or $C_6$–$C_8$ aryloxy. The ring can be mono, di, or trisubstituted by $R^1$, e.g. 3-substituted aniline, 3,4-disubstituted aniline, 3,4,5-trisubstituted aniline. Preferred are substituents which are electron donating. Representative examples of $R^1$ are hydrogen, methoxy, ethoxy, phenoxy, chloro, bromo, fluoro, trifluoromethyl, phenyl, methyl, ethyl, benzyl, and the like.

Representative examples of aromatic amines include p-methoxyaniline, m-ethoxyaniline, p-chloroaniline, p-methylaniline, p-ethoxyaniline, p-methoxyaniline, m-trifluoroaniline, p-benzylaniline, p-phenylaniline and the like. Preferred is p-methoxyaniline, i.e. p-anisidine.

The aromatic amine is added in portions to the dissolved glyoxal II to form the imine IV until substantially all of the glyoxal II has been consumed, as monitored, for example, by conventional gas chromatographic analysis.

The obtained imine IV is obtained as a solid or as an oil and is isolated and purified by conventional means.

The imine can be used directly without extensive purification in the subsequent ketene-imine 2+2 ring closure to form a beta lactam as described above.

Yields of the imine IV are in the range of 70 to 90% based on starting arylmethylketone.

Apparatus for conducting the reaction is conventional in the art.

The following example is illustrative of carrying out the invention process and should not be construed as being a limitation on the scope or spirit of the instant invention.

EXAMPLE 1

Aqueous hydrobromic acid (48%, 17.7 mL, 0.16 mol) was added to a solution of acetophenone (25.0 g, 0.21 mol) in dimethyl sulfoxide (88 mL, 1.25 mol) contained in a round bottom flask fitted with a short path distillation head, a thermometer, and a collection flask. The addition of hydrobromic acid is exothermic. On this scale the internal temperature rose to 49° C. The resulting solution was heated to 80° C. (bath temperature) and the evolved dimethyl sulfide was removed by distillation (head temperature 35°–40° C.). The progress of the reaction was followed by reverse-phase HPLC. HPLC conditions: 25 cm Zorbax C8 column; elution with 70% water (containing 0.2% v/v $H_3PO_4$): 30% acetonitrile at 2 mL/min; uv detection at 210 nm; retention times (min): dimethyl sulfoxide (1.6), phenylglyoxal (2.5), dimethyl sulfide (4.4), acetophenone (7.2). After 4 hours, the reaction was cooled to room temperature and the remaining dimethyl sulfide was removed with a nitrogen sweep. The solution was poured into methylene chloride (500 mL), dried over sodium sulfate, and neutralized with solid sodium bicarbonate. The filtered phenylglyoxal solution, containing 3A molecular sieves (4–8 mesh), was treated in portions with p-anisidine (18.24 g, 0.15 mol) until the phenylglyoxal was completely consumed as determined by GC analysis. GC conditions: 25 m methyl silicone fluid capillary column, split mode injection system with helium carrier and FID detector. Initial temperature 100° C. for 3 min, then 30° C./min to 230° C., for 20 min. Retention times (min): phenylglyoxal (4.0), phenacylimine (12.2). The solution was filtered and concentrated in vacuo. The crude phenacylimine was diluted with 1:1 hexanes:ethyl acetate (500 mL), washed with 10% aqueous sodium bicarbonate solution (2×200 mL), saturated aqueous sodium chloride solution (150 mL), and dried over magnesium sulfate. The phenacylimine solution was then filtered and concentrated in vacuo to give 38.5 g of an orange oil, which solidified on standing in a freezer. $^1$H NMR (300 MHz, CDCl$_3$, TMS) & 8.36(s,1H), 8.30(m,2H), 7.62(m,1H), 7.50(m,2H), 7.41(m,2H), 6.97(m,2H), 3.86(s,3H); IR (CHCl$_3$) 3000,1650,1590, 1580,1507,1250 cm$^{-1}$. This material was approximatey 93% pure (71% yield from acetophenone) and was suitable for use in ketene-imine cycloadditions.

What is claimed is:

1. A process for preparing the 1,2-iminoketone

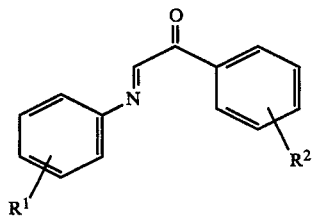
(IV)

comprising the steps of
(a) contacting the arylketone

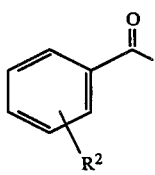
(I)

wherein R$^2$ is H, C$_1$-C$_4$ linear or branched alkyl, C$_6$-C$_8$ aryl, benzyl, nitro, halo, trifluoromethyl, C$_1$-C$_4$ linear or branched alkoxy or C$_6$-C$_8$ aryloxy, with aqueous HBr in DMSO solvent, at a temperature in the range of 50° to 150° C., thereby evolving DMS gas, for a sufficient time to substantially form the glyoxal II:

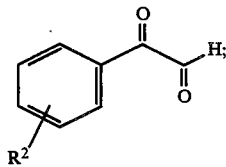
(II)

(b) contacting said glyoxal II from step a) with an aromatic amine III:

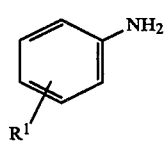
(III)

where R$^1$ is hydrogen, C$_1$-C$_4$ linear or branched alkyl, C$_6$-C$_8$ aryl, benzyl, nitro, halo, trifluoromethyl, C$_1$-C$_4$ linear or branched alkoxy or C$_6$-C$_8$ aryloxy, to form said 1,2-iminoketone.

2. The process of claim 1 wherein said temperature in step (a) is in the range of 70° to 80° C.

3. The process of claim 1 wherein step (a) is conducted until 96–99% of the theoretical yield of the glyoxal II is reached.

4. The process of claim 1 wherein R$^1$ is methoxy, ethoxy, hydrogen, methyl or ethyl.

5. The process of claim 1 wherein R$^2$ is H, chloro, fluoro, methoxy, trifluoromethyl, methyl, t-butyl, phenyl, benzyl, or phenoxy.

6. The process of claim 1 wherein said glyoxal II in step (b) is not isolated and is mixed with said DMSO solvent in step (a) with an inert, water-immiscible, organic solvent prior to step (b).

7. The organic solvent of claim 6 being a C$_1$-C$_8$ linear or branched alkane, C$_5$-C$_8$ cyclic alkane, said alkane optionally containing 1–6 halogens, C$_2$-C$_8$ linear or cyclic ether or C$_6$-C$_8$ aromatic hydrocarbon.

8. The organic solvent of claim 7 being methylene dichloride.

9. The process of claim 1 wherein DMS gas is distilled off during step (a).

10. A process for preparing the 1,2-iminoketone

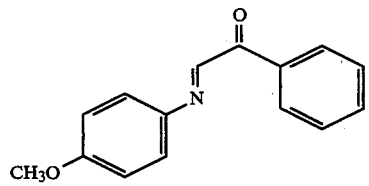
(5)

comprising the steps:
(a) contacting acetophenone with aqueous HBr in DMSO solvent at a temperature in the range of 70° to 80° C. for a sufficient time to substantially form phenylglyoxal;
(b) mixing said phenylglyoxal in the DMSO solvent in step a) with an inert, water-immiscible, organic solvent;
(c) contacting said phenylglyoxal in said organic solvent/DMSO solution from step (b) with p-anisidine to form the product p-anisidine phenylglyoxalimine 5.

11. The process of claim 1, wherein the concentration of arylketone in DMSO solvent is from about 2 to 2.5 moles/liter.

12. The process of claim 11, wherein the molar ratio of HBr to arylketone is about 0.5 to 1.0 in DMSO.

13. The process of claim 10, wherein the concentration of acetophinone in DMSO solvent is from about 1 to 5 moles/liter.

14. The process of claim 10, wherein the molar ratio of HBr to acetophinone in the DMSO solvent is about 0.5 to 1.0.

* * * * *